United States Patent [19]

Lacefield

[11] 4,190,725
[45] Feb. 26, 1980

[54] 5,6-DIARYL-1,2,4-TRIAZINES

[75] Inventor: William B. Lacefield, Indianapolis, Ind.

[73] Assignee: Eli Lilly and Company, Indianapolis, Ind.

[21] Appl. No.: 952,375

[22] Filed: Oct. 18, 1978

Related U.S. Application Data

[63] Continuation of Ser. No. 665,593, Mar. 10, 1976, abandoned, which is a continuation-in-part of Ser. No. 438,156, Jan. 31, 1974, Pat. No. 3,948,894.

[51] Int. Cl.² ............................................. C07D 253/06
[52] U.S. Cl. ....................................................... 544/182
[58] Field of Search ........................................... 544/182

[56] References Cited

U.S. PATENT DOCUMENTS

| | | | |
|---|---|---|---|
| 3,948,894 | 4/1976 | Lacefield | 260/249.5 |
| 3,979,516 | 9/1976 | Lacefield | 424/249 |
| 3,989,831 | 11/1976 | Lacefield | 424/249 |
| 4,008,232 | 2/1977 | Lacefield | 260/247.1 M |
| 4,013,654 | 3/1977 | Lacefield | 260/248 |
| 4,018,923 | 4/1977 | Lacefield | 424/249 |
| 4,021,553 | 5/1977 | Lacefield | 424/249 |

FOREIGN PATENT DOCUMENTS 50-00029  1/1975  Japan .

Primary Examiner—John M. Ford
Attorney, Agent, or Firm—Kathleen R. S. Page; Everet F. Smith

[57] ABSTRACT

5,6-Diaryl-1,2,4-triazines, topically-active anti-inflammatory agents, having the formula,

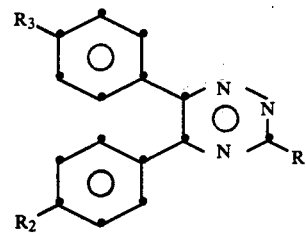

wherein R is hydrogen or $-(X)_n R_1$, in which X is either O or S, n is an integer which is either 0 or 1, and $R_1$ is $C_1$–$C_8$ alkyl, $C_7$–$C_8$ aralkyl, $C_3$–$C_8$ cycloalkyl, or $C_4$–$C_8$ (cycloalkyl)alkyl; and $R_2$ and $R_3$ independently are $C_1$–$C_3$ alkoxy or di($C_1$–$C_3$ alkyl)amino; with the proviso that when $R_2$ and $R_3$ both are methoxy, R cannot be H or methylthio; and the pharmaceutically-acceptable acid addition salts of basic members thereof.

5 Claims, No Drawings

5,6-DIARYL-1,2,4-TRIAZINES

CROSS-REFERENCE TO RELATED APPLICATIONS

This is a continuation of application Ser. No. 665,593, filed Mar. 10, 1976, and abandoned after the filing of this application. Application Ser. No. 665,593 was, in turn, a continuation-in-part of then copending application Ser. No. 438,156, filed Jan. 31, 1974, and issued Apr. 6, 1976, as U.S. Pat. No. 3,948,894.

BACKGROUND OF THE INVENTION

This invention relates to anti-inflammatory 5,6-diaryl-1,2,4-triazines. More particularly, this invention relates to topically-active anti-inflammatory 5,6-diaryl-1,2,4-triazines.

Inflammation is an essentially protective and normal response to injury, although the etiology and pathogenesis of many inflammatory conditions remain obscure. In general, anti-inflammatory agents are employed primarily to relieve the symptoms of inflammation. In such symptomatic therapy, topically-applied anti-inflammatory agents present special problems. Inflammatory conditions calling for the topical application of an anti-inflammatory agent are almost exclusively treated with steroids. Topically-applied steroids, however, may carry considerable systemic toxicity. Thus, the need continues for safer, better tolerated topically-active anti-inflammatory agents.

SUMMARY OF THE INVENTION

In accordance with the present invention, 5,6-diaryl-1,2,4-triazines are provided having the formula,

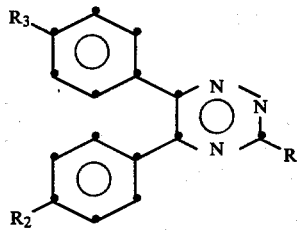

wherein R is hydrogen or $-(X)_nR_1$, in which X is either O or S, n is an integer which is either 0 or 1, and $R_1$ is $C_1-C_8$ alkyl, $C_7-C_8$ aralkyl, $C_3-C_8$ cycloalkyl, or $C_4-C_8$ (cycloalkyl)alkyl; and $R_2$ and $R_3$ independently are $C_1-C_3$ alkoxy or di($C_1-C_3$ alkyl)amino; with the proviso that when $R_2$ and $R_3$ both are methoxy, R cannot be H or methylthio; and the pharmaceutically-acceptable acid addition salts of basic members thereof.

The compounds of the present invention are useful as anti-inflammatory agents. In particular, all of such compounds are especially useful as topically-active anti-inflammatory agents in warm-blooded mammals, such as guinea pigs, mice, rats, dogs, monkeys, humans, and the like. In addition, those compounds wherein X is O or S and n is 1 are useful as intermediates in the preparation of anti-inflammatory 3-amino-5,6-diaryl-1,2,4-triazines which are disclosed an claimed in copending and commonly-assigned application Ser. No. 438,156, filed Jan. 31, 1974, by William B. Lacefield, now U.S. Pat. No. 3,948,894.

DETAILED DESCRIPTION OF THE INVENTION

The term "$C_1-C_8$ alkyl" includes methyl, ethyl, propyl, isopropyl, butyl, isobutyl, sec-butyl, tert-butyl, pentyl, isopentyl, 1-methylbutyl, 1-ethylpropyl, neopentyl, tert-pentyl, 1,2-dimethylpropyl, hexyl, isohexyl, 2-ethylbutyl, 1-ethyl-1-methylpropyl, heptyl, 2-ethyl-1-methylbutyl, 2,4-dimethylpentyl, octyl, 2-ethylhexyl, 1,1-diethylbutyl, and the like.

The term "$C_7-C_8$ aralkyl" includes benzyl, 2-phenylethyl, p-methylbenzyl, m-methylbenzyl, o-methylbenzyl, and the like.

The term "$C_3-C_8$ cycloalkyl" includes cyclopropyl, 2-butylcyclopropyl, cyclobutyl, 2-ethyl-3-methylcyclobutyl, cyclopentyl, 3-isopropylcyclopentyl, cyclohexyl, 1-methylcyclohexyl, 2,5-dimethylcyclohexyl, cycloheptyl, 5-methylcycloheptyl, cyclooctyl, and the like.

The term "$C_4-C_8$ (cycloalkyl)alkyl" includes cyclopropylmethyl, 3-cyclopropyl-2-methylbutyl, 3-(2-methylcyclobutyl)propyl, 2-cyclopentylethyl, 2-methylcyclohexylmethyl, cycloheptylmethyl, and the like.

The term "$C_1-C_3$ alkoxy" includes methoxy, ethoxy, propoxy, and isopropoxy. The term "$C_1-C_3$ alkyl" includes methyl, ethyl, propyl, and isopropyl.

Illustrative of the triazine compounds which are provided by the present invention are the following:

5,6-bis(4-ethoxyphenyl)-1,2,4-triazine,
5,6-bis(4-dimethylaminophenyl)-1,2,4-triazine,
5,6-bis(4-dipropylaminophenyl)-1,2,4-triazine,
5-(4-diethylaminophenyl)-6-(4-methoxyphenyl)-1,2,4-triazine,
5,6-bis(4-methoxyphenyl)-3-methyl-1,2,4-triazine,
3-ethyl-5,6-bis(4-methoxyphenyl)-1,2,4-triazine,
5,6-bis(4-methoxyphenyl)-3-propyl-1,2,4-triazine,
3-isopropyl-5,6-bis(4-methoxyphenyl)-1,2,4-triazine,
3-tert-butyl-5,6-bis(4-methoxyphenyl)-1,2,4-triazine,
3-(1,2-dimethylpropyl)-5,6-bis(4-methoxyphenyl)-1,2,4-triazine,
3-heptyl-5,6-bis(4-methoxyphenyl)-1,2,4-triazine,
5,6-bis(4-ethoxyphenyl)-3-methyl-1,2,4-triazine,
5,6-bis(4-ethoxyphenyl)-3-ethyl-1,2,4-triazine,
5,6-bis(4-ethoxyphenyl)-3-propyl-1,2,4-triazine,
5,6-bis(4-ethoxyphenyl)-3-isopropyl-1,2,4-triazine,
5,6-bis(4-ethoxyphenyl)-3-hexyl-1,2,4-triazine,
3-ethyl-5,6-bis(4-propoxyphenyl)-1,2,4-triazine,
3-(1-methylbutyl)-5,6-bis(4-propoxyphenyl)-1,2,4-triazine,
3-neoheptyl-5,6-bis(4-propoxyphenyl)-1,2,4-triazine,
5,6-bis(4-isopropoxyphenyl)-3-methyl-1,2,4-triazine,
3-sec-butyl-5,6-bis(4-isopropoxyphenyl)-1,2,4-triazine,
5,6-bis(4-isopropoxyphenyl)-3-octyl-1,2,4-triazine,
5-(4-methoxyphenyl)-3-methyl-6-(4-propoxyphenyl)-1,2,4-triazine,
6-(4-ethoxyphenyl)-5-(4-isopropoxyphenyl)-3-(2,3,4-trimethylpentyl)-1,2,4-triazine,
5,6-bis(4-dimethylaminophenyl)-3-methyl-1,2,4-triazine,
5,6-bis(4-dimethylaminophenyl)-3-ethyl-1,2,4-triazine,
5,6-bis(4-dimethylaminophenyl)-3-propyl-1,2,4-triazine,
5,6-bis(4-dimethylaminophenyl)-3-isopropyl-1,2,4-triazine, 5,6-bis(4-dimethylaminophenyl)-3-isopentyl-1,2,4-triazine,
5,6-bis(4-dimethylaminophenyl)-3-(2-ethylhexyl)-1,2,4-triazine,
5,6-bis(4-diethylaminophenyl)-3-methyl-1,2,4-triazine,
5,6-bis(4-diethylaminophenyl)-3-ethyl-1,2,4-triazine,
5,6-bis(4-diethylaminophenyl)-3-propyl-1,2,4-triazine,
5,6-bis(4-diethylaminophenyl)-3-isopropyl-1,2,4-triazine,
5,6-bis(4-diethylaminophenyl)-3-(2,2,3-trimethylbutyl)-1,2,4-triazine,
5,6-bis(4-dipropylaminophenyl)-3-methyl-1,2,4-triazine,
3-sec-butyl-5,6-bis(4-dipropylaminophenyl)-1,2,4-triazine,
5,6-bis(4-dipropylaminophenyl)-3-(2-ethylbutyl)-1,2,4-triazine,
5,6-bis(4-diisopropylaminophenyl)-3-ethyl-1,2,4-triazine,
5,6-bis(4-diisopropylaminophenyl)-3-tert-pentyl-1,2,4-triazine,
5,6-bis(4-diisopropylaminophenyl)-3-(2,2,4-trimethylpentyl)-1,2,4-triazine,
6-(4-diisopropylaminophenyl)-5-(4-dimethylaminophenyl)-3-neoheptyl-1,2,4-triazine,
5-(4-diisopropylaminophenyl)-6-(4-ethoxyphenyl)-3-methyl-1,2,4-triazine,
3-benzyl-5,6-bis(4-methoxyphenyl)-1,2,4-triazine,
5,6-bis(4-methoxyphenyl)-3-(m-methylbenzyl)-1,2,4-triazine,
5,6-bis(4-ethoxyphenyl)-3-(2-phenylethyl)-1,2,4-triazine,
3-(1-phenylethyl)-5,6-bis(4-propoxyphenyl)-1,2,4-triazine,
5,6-bis(4-isopropoxyphenyl)-3-(o-methylbenzyl)-1,2,4-triazine,
3-benzyl-5-(4-methoxyphenyl)-6-(4-propoxyphenyl)-1,2,4-triazine,
5,6-bis(4-diethylaminophenyl)-3-(p-methylbenzyl)-1,2,4-triazine,
5-(4-diethylaminophenyl)-6-(4-diisopropylaminophenyl)-3-(2-phenylethyl)-1,2,4-triazine,
3-benzyl-6-(4-diethylaminophenyl)-5-(4-ethoxyphenyl)-1,2,4-triazine,
3-cyclopropyl-5,6-bis(4-methoxyphenyl)-1,2,4-triazine,
3-cyclopentyl-5,6-bis(4-propoxyphenyl)-1,2,4-triazine,
3-cyclobutyl-5-(4-ethoxyphenyl)-6-(4-methoxyphenyl)-1,2,4-triazine,
3-cyclooctyl-5,6-bis(4-dimethylaminophenyl)-1,2,4-triazine,
5,6-bis(4-dipropylaminophenyl)-3-(2-ethylcyclopropyl)-1,2,4-triazine,
5-(4-diethylaminophenyl)-6-(4-dipropylaminophenyl)-3-(2-ethylcyclobutyl)-1,2,4-triazine,
3-cycloheptyl-6-(4-dipropylaminophenyl)-5-(4-methoxyphenyl)-1,2,4-triazine.
3-(2-cyclohexylethyl)-5,6-bis(4-ethoxyphenyl)-1,2,4-triazine,
3-cyclobutylmethyl-5,6-bis(4-isopropoxyphenyl)-1,2,4-triazine,
5-(4-ethoxyphenyl)-6-(4-isopropoxyphenyl)-3-(2-methylcyclohexylmethyl)-1,2,4-triazine,
3-cyclopropylmethyl-5,6-bis(4-diethylaminophenyl)-1,2,4-triazine,
5,6-bis(4-dipropylaminophenyl)-3-[2-(2-methylcyclobutyl)ethyl]-1,2,4-triazine,
3-cycloheptylmethyl-5,6-bis(4-diisopropylaminophenyl)-1,2,4-triazine,
3-(1-cyclohexylethyl)-5-(4-diethylaminophenyl)-6-(4-dimethylaminophenyl)-1,2,4-triazine,
3-cyclopentylmethyl-5-(4-diethylaminophenyl)-6-(4-ethoxyphenyl)-1,2,4-triazine,
3-methoxy-5,6-bis(4-methoxyphenyl)-1,2,4-triazine,
3-ethoxy-5,6-bis(4-methoxyphenyl)-1,2,4-triazine,
5,6-bis(4-methoxyphenyl)-3-propoxy-1,2,4-triazine,
3-isopropoxy-5,6-bis(4-methoxyphenyl)-1,2,4-triazine,
3-hexyloxy-5,6-bis(4-methoxyphenyl)-1,2,4-triazine,
3-(1,2-diethylbutoxy)-5,6-bis(4-methoxyphenyl)-1,2,4-triazine,
5,6-bis(4-ethoxyphenyl)-3-methoxy-1,2,4-triazine,
3-ethoxy-5,6-bis(4-ethoxyphenyl)-1,2,4-triazine,
5,6-bis(4-ethoxyphenyl)-3-propoxy-1,2,4-triazine,
5,6-bis(4-ethoxyphenyl)-3-isopropoxy-1,2,4-triazine,
5,6-bis(4-ethoxyphenyl)-3-neopentyloxy-1,2,4-triazine,
5,6-bis(4-ethoxyphenyl)-3-(1-ethyl-2-methylbutoxy)-1,2,4-triazine,
3-methoxy-5,6-bis(4-propoxyphenyl)-1,2,4-triazine,
3-ethoxy-5,6-bis(4-propoxyphenyl)-1,2,4-triazine,
3-propoxy-5,6-bis(4-propoxyphenyl)-1,2,4-triazine,
3-hexyloxy-5,6-bis(4-propoxyphenyl)-1,2,4-triazine,
3-ethoxy-5,6-bis(4-isopropoxyphenyl)-1,2,4-triazine,
3-(1-ethylbutoxy)-5,6-bis(4-isopropoxyphenyl)-1,2,4-triazine,
3-(2-ethylhexyloxy)-5,6-bis(4-isopropoxyphenyl)-1,2,4-triazine,
6-(4-ethoxyphenyl)-5-(4-isopropoxyphenyl)-3-(2,2,3-trimethylbutoxy)-1,2,4-triazine,
5,6-bis(4-dimethylaminophenyl)-3-methoxy-1,2,4-triazine,
5,6-bis(4-dimethylaminophenyl)-3-ethoxy-1,2,4-triazine,
5,6-bis(4-dimethylaminophenyl)-3-propoxy-1,2,4-triazine,
5,6-bis(4-dimethylaminophenyl)-3-isopropoxy-1,2,4-triazine,
3-butoxy-5,6-bis(4-dimethylaminophenyl)-1,2,4-triazine,
5,6-bis(4-dimethylaminophenyl)-3-isoheptyloxy-1,2,4-triazine,
5,6-bis(4-diethylaminophenyl)-3-methoxy-1,2,4-triazine,
5,6-bis(4-diethylaminophenyl)-3-ethoxy-1,2,4-triazine,
5,6-bis(4-diethylaminophenyl)-3-propoxy-1,2,4-triazine,
5,6-bis(4-diethylaminophenyl)-3-isopropoxy-1,2,4-triazine,
5,6-bis(4-diethylaminophenyl)-3-pentyloxy-1,2,4-triazine,
5,6-bis(4-dipropylaminophenyl)-3-methoxy-1,2,4-triazine,
3-tert-butoxy-5,6-bis(4-dipropylaminophenyl)-1,2,4-triazine,
5,6-bis(4-dipropylaminophenyl)-3-neoheptyloxy-1,2,4-triazine,
5,6-bis(4-diisopropylaminophenyl)-3-methoxy-1,2,4-triazine,
3-butoxy-5,6-bis(4-diisopropylaminophenyl)-1,2,4-triazine, 5,6-bis(4-diisopropylaminophenyl)-3-(1-ethyl-1-methylpropoxy)-1,2,4-triazine,
5-(4-diisopropylaminophenyl)-6-(4-dimethylaminophenyl)-3-methoxy-1,2,4-triazine,
6-(4-diethylaminophenyl)-3-ethoxy-5-(4-methoxyphenyl)-1,2,4-triazine,
3-benzyloxy-5,6-bis(4-ethoxyphenyl)-1,2,4-triazine,
5,6-bis(4-isopropoxyphenyl)-3-(2-phenylethoxy)-1,2,4-triazine,
5-(4-ethoxyphenyl)-3-(o-methylbenzyloxy)-6-(4-propoxyphenyl)-1,2,4-triazine,
3-benzyloxy-5,6-bis(4-dimethylaminophenyl)-1,2,4-triazine,
5-(4-diethylaminophenyl)-6-(4-diisopropylaminophenyl)-3-(1-phenylethoxy)-1,2,4-triazine,
6-(4-dipropylaminophenyl)-5-(4-methoxyphenyl)-3-(m-methylbenzyloxy)-1,2,4-triazine,
3-cycloheptyloxy-5,6-bis(4-ethoxyphenyl)-1,2,4-triazine,
3-cyclobutyloxy-5,6-bis(4-isopropoxyphenyl)-1,2,4-triazine,
3-cyclohexyloxy-5-(4-ethoxyphenyl)-6-(4-propoxyphenyl)-1,2,4-triazine,
5,6-bis(4-diethylaminophenyl)-3-(2-methylcyclopentyloxy)-1,2,4-triazine,
3-cyclobutyloxy-5,6-bis(4-diisopropylaminophenyl)-1,2,4-triazine,
3-cyclohexyloxy-6-(4-diethylaminophenyl)-5-(4-dimethylaminophenyl)-1,2,4-triazine,
5-(4-dipropylaminophenyl)-6-(4-ethoxyphenyl)-3-(2-ethyl-3-methylcyclopentyloxy)-1,2,4-triazine,
5,6-bis(4-methoxyphenyl)-3-(2-methylcyclobutylmethoxy)-1,2,4-triazine,
3-(3-methylcyclopentylmethoxy)-5,6-bis(4-propoxyphenyl)-1,2,4-triazine.
3-cyclohexylmethoxy-5,6-bis(4-dimethylaminophenyl)-1,2,4-triazine,
3-cyclopropylmethoxy-5,6-bis(4-dipropylaminophenyl)-1,2,4-triazine,
5-(4-diethylaminophenyl)-6-(4-dimethylaminophenyl)-3-[2-(2-ethylcyclobutyl)ethoxy]-1,2,4-triazine,
3-(4-cyclopropylbutoxy)-6-(4-dipropylaminophenyl)-5-(4-isopropoxyphenyl)-1,2,4-triazine,
3-ethylthio-5,6-bis(4-methoxyphenyl)-1,2,4-triazine,
5,6-bis(4-methoxyphenyl)-3-propylthio-1,2,4-triazine,
3-isopropylthio-5,6-bis(4-methoxyphenyl)-1,2,4-triazine,
3-butylthio-5,6-bis(4-methoxyphenyl)-1,2,4-triazine,
5,6-bis(4-methoxyphenyl)-3-neoheptylthio-1,2,4-triazine,
5,6-bis(4-ethoxyphenyl)-3-methylthio-1,2,4-triazine,
5,6-bis(4-ethoxyphenyl)-3-ethylthio-1,2,4-triazine,
5,6-bis(4-ethoxyphenyl)-3-propylthio-1,2,4-triazine,
5,6-bis(4-ethoxyphenyl)-3-isopropylthio-1,2,4-triazine,
5,6-bis(4-ethoxyphenyl)-3-(3-methylpentylthio)-1,2,4-triazine,
5,6-bis(4-ethoxyphenyl)-3-octylthio-1,2,4-triazine,
3-methylthio-5,6-bis(4-propoxyphenyl)-1,2,4-triazine,
3-ethylthio-5,6-bis(4-propoxyphenyl)-1,2,4-triazine,
5,6-bis(4-propoxyphenyl)-3-propylthio-1,2,4-triazine,
3-isopropylthio-5,6-bis(4-propoxyphenyl)-1,2,4-triazine,
3-(1,2-dimethylpropylthio)-5,6-bis(4-propoxyphenyl)-1,2,4-triazine,
3-heptyloxy-5,6-bis(4-propoxyphenyl)-1,2,4-triazine,
5,6-bis(4-isopropoxyphenyl)-3-methylthio-1,2,4-triazine,
5,6-bis(4-isopropoxyphenyl)-3-pentylthio-1,2,4-triazine,
6-(4-isopropoxyphenyl)-3-methylthio-5-(4-propoxyphenyl)-1,2,4-triazine,
5,6-bis(4-dimethylaminophenyl)-3-methylthio-1,2,4-triazine,
5,6-bis(4-dimethylaminophenyl)-3-ethylthio-1,2,4-triazine,
5,6-bis(4-dimethylaminophenyl)-3-propylthio-1,2,4-triazine,
5,6-bis(4-dimethylaminophenyl)-3-isopropylthio-1,2,4-triazine,
5,6-bis(4-dimethylaminophenyl)-3-isoheptylthio-1,2,4-triazine,
5,6-bis(4-diethylaminophenyl)-3-methylthio-1,2,4-triazine,
5,6-bis(4-diethylaminophenyl)-3-ethylthio-1,2,4-triazine,
5,6-bis(4-diethylaminophenyl)-3-propylthio-1,2,4-triazine,
5,6-bis(4-diethylaminophenyl)-3-isopropylthio-1,2,4-triazine,
5,6-bis(4-diethylaminophenyl)-3-pentylthio-1,2,4-triazine,
5,6-bis(4-diethylaminophenyl)-3-(1,1-dimethylhexylthio)-1,2,4-triazine,
5,6-bis(4-dipropylaminophenyl)-3-ethylthio-1,2,4-triazine,
3-(1,2-dimethylpropylthio)-5,6-bis(4-dipropylaminophenyl)-1,2,4-triazine,
5,6-bis(4-dipropylaminophenyl)-3-(1-ethyl-2-methylbutylthio)-1,2,4-triazine,
5,6-bis(4-diisopropylaminophenyl)-3-ethylthio-1,2,4-triazine,
5,6-bis(4-diisopropylaminophenyl)-3-isobutylthio-1,2,4-triazine,
5,6-bis(4-diisopropylaminophenyl)-3-(2-methylpentylthio)-1,2,4-triazine,
6-(4-diethylaminophenyl)-5-(4-diisopropylaminophenyl)-3-isohexylthio-1,2,4-triazine,
5-(4-dimethylaminophenyl)-6-(4-isopropoxyphenyl)-3-(2-isopropyl-3-methylbutylthio)-1,2,4-triazine,
3-benzylthio-5,6-bis(4-methoxyphenyl)-1,2,4-triazine,
6-(4-isopropoxyphenyl)-5-(4-methoxyphenyl)-3-(2-phenylethylthio)-1,2,4-triazine,
5,6-bis(4-dipropylaminophenyl)-3-(p-methylbenzylthio)-1,2,4-triazine,
6-(4-diethylaminophenyl)-5-(4-dipropylaminophenyl)-3-(o-methylbenzylthio)-1,2,4-triazine,
3-benzylthio-5-(4-dimethylaminophenyl)-6-(4-methoxyphenyl)-1,2,4-triazine,
3-(2-isopropylcyclopentylthio)-5,6-bis(4-methoxyphenyl)-1,2,4-triazine,
3-(2-ethylcyclobutylthio)-5,6-bis(4-isopropoxyphenyl)-1,2,4-triazine,
3-cyclobutylthio-6-(4-ethoxyphenyl)-5-(4-methoxyphenyl)-1,2,4-triazine,
3-cyclopropylthio-5,6-bis(4-dimethylaminophenyl)-1,2,4-triazine,
5,6-bis(4-diethylaminophenyl)-3-(2-ethylcyclohexylthio)-1,2,4-triazine,
3-cyclopentylthio-5-(4-dimethylaminophenyl)-6-(4-dipropylaminophenyl)-1,2,4-triazine,
6-(4-dipropylaminophenyl)-5-(4-ethoxyphenyl)-3-(2-methylcyclopropylthio)-1,2,4-triazine,
3-(3-methylcyclohexylmethylthio)-5,6-bis(4-methoxyphenyl)-1,2,4-triazine, 3-(2-cyclobutylethylthio)-5,6-bis(4-ethoxyphenyl)-1,2,4-triazine, 3-cycloheptylmethylthio-6-(4-isopropoxyphenyl)-5-(4-propoxyphenyl)-1,2,4-triazine, 3-cyclopropylmethylthio-5,6-bis(4-dimethylaminophenyl)-1,2,4-triazine, 5,6-bis(4-dipropylaminophenyl)-3-[2-(1-methylcyclopentyl)ethylthio]-1,2,4-triazine, 5-(4-diethylaminophenyl)-6-(4-dipropylaminophenyl)-3-(2,3-dimethylcyclopentylmethylthio)-1,2,4-triazine, 3-(2-cyclobutylbutylthio)-6-(4-dimethylaminophenyl)-5-(4-methoxyphenyl)-1,2,4-triazine, and the like, and the pharmaceutically-acceptable acid addition salts of the basic triazines.

The preferred triazines are those wherein $R_2$ and $R_3$ in the above-defined formula are $C_1$–$C_3$ alkoxy. More preferably, $R_2$ and $R_3$ will be the same, and most preferably are methoxy. With respect to the substituent in the 3-position, the preferred groups are $C_1$–$C_8$ alkyl (R is —(X)$_n$R$_1$, n is 0, and R$_1$ is $C_1$–$C_8$ alkyl), $C_1$–$C_8$ alkoxy (R is —(X)$_n$R$_1$, n is 1, X is O and R$_1$ is $C_1$–$C_8$ alkyl), and $C_2$–$C_8$ alkylthio (R is —(X)$_n$R$_1$, n is 1, X is S, and R$_1$ is $C_2$–$C_8$ alkyl). More preferably, the 3-substituent is $C_1$–$C_8$ alkyl or $C_1$–$C_8$ alkoxy. Most preferably, the 3-substituent is $C_1$–$C_3$ alkyl or $C_1$–$C_3$ alkoxy.

Examples of such preferred, more preferred, and most preferred triazines are included in the above list of illustrative triazines.

The compounds of the present invention are prepared by a variety of methods known to those having ordinary skill in the art. Starting materials and intermediates also are prepared by known methods. The preparation of 5,6-diaryl-1,2,4-triazines is described generally by J. G. Erickson in "The 1,2,3- and 1,2,4-Triazines, Tetrazines and Pentazines," The Chemistry of Heterocyclic Compounds, Vol. 10, Interscience Publishers, Inc., New York, N.Y., 1956, Chapter II, pp. 44–84. The 5,6-diaryl-1,2,4-triazines which are unsubstituted in the 3-position can be prepared by the catalytic reduction of the corresponding 3-chlorotriazines.

The specific procedure employed to prepare a given 3-substituted-5,6-diaryl-1,2,4-triazine in part is dependent upon the substituent in the 3-position. For example, 3-alkyl-, 3-aralkyl-, 3-cycloalkyl-, and 3-(cycloalkyl)alkyl-5,6-diaryl-1,2,4-triazines can be prepared directly by the cyclization of acylhydrazones of α-diketones by ammonium acetate in hot acetic acid under controlled conditions; see, e.g., C. M. Atkinson and H. D. Cossey, *J. Chem. Soc.*, 1962, 1805 [*Chem. Abstr.*, 57:4662i (1962)]. Such triazines also can be prepared from 3-chloro-5,6-diaryl-1,2,4-triazines by the procedure of E. C. Taylor and S. F. Martin [*J. Amer. Chem. Soc.*, 94, 2874 (1972)] which involves the nucleophilic displacement of chlorine by a Wittig reagent which may be generated in situ from an alkyl-, aralkyl-, cycloalkyl-, or (cycloalkyl)alkyltriarylphosphonium halide.

3-Chloro-5,6-diaryl-1,2,4-triazines also can be employed to prepare the 3-alkoxy, 3-aralkoxy, 3-cycloalkoxy-, 3-(cycloalkyl)alkoxy-, 3-alkylthio-, 3-aralkylthio-, 3-cycloalkylthio-, and 3-(cycloalkyl)alkylthio-5,6-diaryl-1,2,4-triazines via the nucleophilic displacement of chlorine by the appropriate alcohol or thiol. The 3-alkylthio-, 3-aralkylthio-, 3-cycloalkylthio-, and 3-(cycloalkyl)alkylthio- compounds can be converted to the 3-alkoxy-, 3-aralkoxy-, 3-cycloalkoxy-, and 3-(cycloalkyl)alkoxy-5,6-diaryl-1,2,4-triazines, again via nucleophilic displacement by the appropriate alcohol. The 3-alkylthio-, 3-aralkylthio-, 3-cycloalkylthio-, and 3-(cycloalkyl)alkylthiotriazines in many cases can be prepared by treating the appropriate 3-mercapto-5,6-diaryl-1,2,4-triazine with the appropriate hydrocarbyl halide in the presence of base, particularly when the hydrocarbyl halide is primary or secondary.

3-Chloro-5,6-diaryl-1,2,4-triazines are readily obtained by treating the appropriate 3-hydroxytriazine with phosphorus oxychloride. 3-Hydroxy- and 3-mercapto-5,6-diaryl-1,2,4-triazines in turn can be prepared by condensing an appropriate benzil with semicarbazide or thiosemicarbazide, respectively.

The required benzils are prepared by the oxidation of the corresponding benzoins with copper sulfate in pyridine; see H. T. Clarke and E. E. Driger, *Org. Synthesis, Coll.* Vol. I, 87 (1941). The benzoins are prepared by the condensation of aromatic aldehydes with cyanide ion; see W. S. Ide and J. S. Buck, *Org. Reactions*, 4, 269 (1948).

Another approach to the compounds of the present invention involves the use of benzils having substituents which can be displaced to give the desired $R_2$ or $R_3$ substituent. For example, the halogen on the phenyl ring at the 5-position in 5-(4-halophenyl)-6-aryl-1,2,4-triazines can be displaced with an alcohol or a dialkylamine to give the corresponding 5-(4-alkoxyphenyl)- or 5-(4-dialkylaminophenyl)- compound, respectively.

The use of two different aromatic aldehydes in the benzoin synthesis leads to unsymmetrical benzils. That is, in a benzil of the formula,

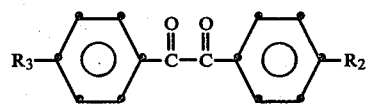

wherein $R_2$ and $R_3$ are as described hereinbefore, $R_2$ and $R_3$ are different. The use of an unsymmetrical benzil may result in the preparation of a mixture of triazine isomers. For example, the condensation of 4-dimethylamino-4'-methoxybenzil with thiosemicarbazide gives a mixture of 5-(4-dimethylaminophenyl)-6-(4-methoxyphenyl)-1,2,4-triazine-3-thiol and 6-(4-dimethylaminophenyl)-5-(4-methoxyphenyl)-1,2,4-triazine-3-thiol It will be recognized by those skilled in the art that mixtures of triazine isomers are separable by known methods, such as fractional crystallization and chromatography. The isomer separation may be effected upon intermediate mixtures or delayed until the final product stage.

Certain of the 5,6-diaryl-1,2,4-triazines described herein are sufficiently basic to form acid addition salts, especially when the triazine contains one or more dialkylamino groups on the phenyl rings. "Pharmaceutically-acceptable" acid addition salts are well known to those skilled in the art and in general are formed by reacting in a mutual solvent a stoichiometric amount of a suitable acid with a basic triazine. Such salts should not be substantially more toxic to warm-blooded animals than the traizines. While the choice of a salt-forming acid is not critical, in some instances a particular acid may result in a salt having special advantages, such as ready solubility, ease of crystallization, and the like. Representative and suitable acids include, among others, the following: hydrochloric, hydrobromic, hydriodic, sulfuric, nitric, phosphoric, methanesulfonic, p-toluenesulfonic, and the like.

A modification of the method of Winder was used to measure the anti-inflammatory activites of the compounds of the present invention; see C. V. Winder, et al., *Arch. Int. Pharmacodyn.*, 116, 261 (1958). Albino guinea pigs of either sex, weighing 225-300 grams, were shaved on the back and chemically depilated (Nair ® Lotion Hair Remover, Carter Products, N.Y., N.Y.) 18-20 hours before exposure to ultraviolet light. The animals, in groups of four and bearing identifying ear tags, were treated by applying to an area of skin of about 12 cm.² a solution of test compound dissolved in 0.1 cc. of ethanol. The control treatment consisted of administering only the drug vehicle, ethanol, to a group of four animals. Groups of four animals each were given different treatment levels of test compound to obtain dose responses. Random order and blind administration of the test compounds were employed; drug identification was not made until after all animals were graded. Immediately prior to drug application, the animals were exposed in groups of four to a high-intensity ultraviolet light for a measured period of time (usually 4-7 seconds). The ultraviolet light source, a Hanovia Lamp (Kroymayer-Model 10), was placed in contact with the skin of the animal's back. A gummed notebook paper reinforcement was affixed to the lamp lens to provide an unexposed area of contrast for grading the erythema. Beginning one hour after exposure and thereafter at half-hour intervals for another 1½ hours, the degree of resulting erythema was graded by an arbiturary scoring system based upon the degree of contrast and redness formed. Anti-inflammatory agents delay the development of the erythema and usually have their greatest effect at the initial grading periods. The scores were, therefore, weighted by factors of 4, 3, 2, and 1 at the 1.0, 1.5, 2.0, and 2.5 hour scoring times, respectively. The erythema was graded as follows:

| Score | Erythema Scoring System Appearance of Exposed Area |
|---|---|
| 0 | No redness and no contrast |
| 1 | Slight redness with a faint reinforcement outline |
| 2 | Slight to moderate redness with a distinct outline |
| 3 | Marked redness with a distinct circular outline |

Total scores from each treatment group of four guinea pigs were compared to the control treatment, and the percent inhibition was calculated as follows:

$$100 \times \frac{\text{Control Score} - \text{Treatment Score}}{\text{Control Score}} = \text{Percent Inhibition}$$

A dose-response graph was obtained by plotting dose versus percent inhibition, the points representing the average of each treatment group of four guinea pigs. The dose ($ED_{50}$) in micrograms per 12 cm.² (mcg./12 cm.²) which produced a 50% inhibition of the erythemic response for the particular compound tested was obtained in several instances by extrapolation. Table I below summarizes the results obtained from testing representative compounds of the invention by the foregoing method. The plotted or calculated $ED_{50}$ for the particular compound tested, where available, is given in the last column of Table I.

Table I

Erythemic response inhibition of 5,6-Diaryl-1,2,4-triazines

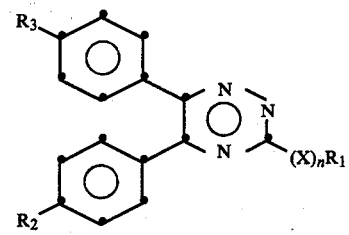

| | | | | | Inhibition | | |
|---|---|---|---|---|---|---|---|
| $R_1$ | X | n | $R_2$ | $R_3$ | Dose[a] | %[b] | $ED_{50}$[a] |
| —$CH_3$ | — | 0 | —$OCH_3$ | —$OCH_3$ | — | — | 2.4 |
| —$C_2H_5$ | — | 0 | —$OCH_3$ | —$OCH_3$ | — | — | 4 |
| —$CH_3$ | O | 1 | —$OCH_3$ | —$OCH_3$ | — | — | 7 |
| —$C_2H_5$ | O | 1 | —$OCH_3$ | —$OCH_3$ | — | — | 3.1 |
| —$CH_3$ | S | 1 | —$OCH_3$ | —$OCH_3$ | — | — | 9 |
| —$C_2H_5$ | S | 1 | —$OCH_3$ | —$OCH_3$ | — | — | 21.3 |
| —$CH(CH_3)_2$ | S | 1 | —$OCH_3$ | —$OCH_3$ | 100 | 35 | — |
| —$C_6H_{13}$ | S | 1 | —$OCH_3$ | —$OCH_3$ | — | — | 37.4 |
| —$CH_2C_6H_5$ | S | 1 | —$OCH_3$ | —$OCH_3$ | 100 | 49 | — |

[a] In mcg./12 cm.²
[b] % Inhibition compared with control

The toxicities of representative compounds of the present invention, determined as the dose ($LD_{50}$) in milligrams per kilogram (mg./kg.) of animal body weight which is lethal to 50 percent of mice treated orally, typically are greater than about 1000 mg./kg., and in some cases are greater than about 1500 mg./kg.

In the utilization of the compounds of this invention, one (or more) of the anti-inflammatory triazines is topically administered to a warm-blooded mammal in an amount sufficient to provide at least about 1 mcg./12 cm.²; such administration can be repeated periodically as needed. Because of the relatively low order of toxicity of such triazines, the maximum level of application is limited only by the esthetics of the mode of administration. As a practical matter, however, such triazines normally need not be administered at a level much above about $10^3$ mcg./12 cm.², although levels of about $10^5$ mcg./12 cm.² or higher can be employed, if desired.

The topical administration of the anti-inflammatory compounds can be made according to any of the well known prior art procedures. Thus, such administration can utilize aerosols, creams, emulsions, lotions, ointments, solutions, and the like. In each case, the compounds to be employed are utilized in combination with one or more adjuvants suited to the particular mode of application. For example, ointments and solutions for topical administration can be formulated with any of a number of pharmaceutically-acceptable carriers, including ethanol, animal and vegetable oils, mixtures of waxes, solid and liquid hydrocarbons, glycols, and the like. Thus, a typical ointment composition comprises the following ingredients per gram of ointment:

| | mg. |
|---|---|
| Triazine | 0.1-100 |
| Polyethylene gylcol 300 (N.F.) | 450-700 |
| Polyethylene gylcol 4000 (U.S.P.) | 300-450 |

The concentration of the anti-inflammatory triazine in the final topical preparation is not critical. In general, such concentration can range from about 0.001 percent to about 50 percent (w/w or w/v), or higher.

The following examples further illustrate the preparations of the compounds of the present invention.

EXAMPLE 1

Preparation of 5,6-Bis(4-methoxyphenyl)-3-methyl-1,2,4-triazine (A) 3-Hydroxy-5,6-bis(4-methoxyphenyl)-1,2,4-triazine Two moles, 540 g., of anisil (4,4'-dimethoxybenzil), 222 g. (2 moles) of semicarbazide hydrochloride, 180 g. (2.2 moles) of sodium acetate, and 2.5 liters of acetic acid were heated at reflux overnight. The cooled reaction mixture was poured into 5 liters of water. The crude solid product was collected by filtration, washed with water, and recrystallized from acetic acid, giving 434 g. of 3-hydroxy-5,6-bis(4-methoxyphenyl)-1,2,4-triazine, m.p. about 272°–274° C.

Analysis: $C_{17}H_{15}N_3O_3$: Calc: C, 66.01; H, 4.89; N, 13.58: Found: C, 65.92; H, 5.04; N, 13.66.

(B) 3-Chloro-5,6-bis(4-methoxyphenyl)-1,2,4-triazine

Ten grams of 3-hydroxy-5,6-bis(4-methoxyphenyl)-1,2,4-triazine and 50 ml. of phosphorous oxychloride were heated at reflux for 1.5 hours. The cooled mixture was poured onto crushed ice and the resultant mixture was extracted with diethyl ether. The extract was washed successively with 2 percent sodium hydroxide and water until the washings were neutral. The ether extract was dried over anhydrous sodium sulfate and evaporated. The residue was taken up in ether, filtered, and the filtrate was evaporated to yield 9.0 g. of 3-chloro-5,6-bis(4-methoxyphenyl)-1,2,4-triazine, m.p. about 130°–132° C.

Analysis: $C_{17}H_{14}ClN_3O_2$: Calc: C, 62.30; H, 4.31; Cl, 10.82; N, 12.82: Found: C, 62.50; H, 4.48; Cl, 10.53; N, 12.99.

(C) 5,6-Bis(4-methoxyphenyl)-3-methyl-1,2,4-triazine

To a slurry of 11.7 g. (0.33 mole) of methyltriphenylphosphonium bromide in 150 ml. of dry tetrahydrofuran at −35° C. was added, over a 15-minute period, 20 ml. (0.033 mole) of n-butyl lithium. The reaction mixture was stirred for one hour. To the reaction mixture at −35° to −40° C. was added over a 10-minute period a solution of 5.7 g. (0.0165 mole) of 3-chloro-5,6-bis(4-methoxyphenyl)-1,2,4-triazine in 50 ml. of tetrahydrofuran. The reaction mixture was allowed to warm to ambient temperature and was stirred overnight. A solution of 1.05 g. (0.0165 mole) of sodium carbonate in 50 ml. of water was added dropwise to the reaction mixture which then was heated at reflux for three hours. The reaction mixture was cooled, poured over ice, and extracted with diethyl ether. The diethyl ether extract was washed with water, dried over anhydrous sodium sulfate, and concentrated. The concentrate was chromatographed over silica gel, with three fractions being collected. After evaporation of solvent, the third fraction solidified, m.p. about 109°–113° C. The solid was identified as 5,6-bis(4-methoxyphenyl)-3-methyl-1,2,4-triazine by nuclear magnetic resonance analysis, mass spectrographic analysis, and elemental microanalysis.

Analysis: $C_{18}H_{17}N_3O_2$: Calc: C, 70.34; H, 5.58; N, 13.67: Found: C, 70.42; H, 5.66; N, 13.33.

EXAMPLE 2

Preparation of 3-Ethyl-5,6-bis(4-methoxyphenyl)-1,2,4-triazine

3-Ethyl-5,6-bis(4-methoxyphenyl)-1,2,4-triazine, m.p. about 73°–75.5° C., was prepared by the method of Example 1(C) using the appropriate phosphonium bromide, except that work-up after diethyl ether extraction was carried out as follows: The diethyl ether extract was washed, dried, and concentrated as in Example 1(C), giving a solid residue which was dissolved in warm petroleum ether/ethyl acetate. The solution was cooled and the solid which precipitated was isolated by filtration. The filtrate solidified and was slurried in petroleum ether. The mixture was filtered and the solid thus obtained (second solid) was recrystallized from petroleum ether/ethyl acetate. The second solid was identified as 3-ethyl-5,6-bis(4-methoxyphenyl)-1,2,4-triazine by nuclear magnetic resonance analysis, mass spectrographic analysis, and elemental microanalysis.

Analysis: $C_{19}H_{19}N_3O_2$: Calc: C, 71.01; H, 5.96; N, 13.08: Found: C, 71.30; H, 6.01; N, 13.10.

EXAMPLE 3

Preparation of 3-Ethylthio-5,6-bis(4-methoxyphenyl)-1,2,4-triazine (A) 3-Mercapto-5,6-bis(4-methoxyphenyl)-1,2,4-triazine One hundred grams of anisil (4,4'-dimethoxybenzil) were added to 600 ml. of acetic acid and the mixture was heated to about 100° C. with stirring. Thiosemicarbazide, 68.4 g., was added and the mixture was heated at reflux for about an hour. The mixture was cooled and the solid product was collected by filtration. The solid was washed successively with acetic acid and water. The product was filtered and air dried to yield 96.3 g. of 3-mercapto-5,6-bis(4-methoxyphenyl)-1,2,4-triazine, m.p. about 233°–236° C.

Analysis: $C_{17}H_{15}N_3O_2S$: Calc: C, 62.75; H, 4.65; N, 12.91; S, 9.85: Found: C, 62.61; H, 4.57; N, 12.66; S, 9.73.

(B) 3-Ethylthio-5,6-bis(4-methoxyphenyl)-1,2,4-triazine

To a mixture of 10 g. (0.031 mole) of 3-mercapto-5,6-bis(4-methoxyphenyl)-1,2,4-triazine in 200 ml. of ethanol was added a solution of 1.3 g. (0.032 mole) of sodium hydroxide in 25 ml. of water. The mixture was stirred until a clear solution was obtained. To the solution was added dropwise over a 10-minute period a solution of 3.4 g. (0.032 mole) of ethyl bromide in 10 ml. of ethanol. The reaction mixture was stirred for 30 minutes. The mixture was poured over ice and extracted with diethyl ether. The diethyl ether extract was washed with water and dried over anhydrous sodium sulfate. The diethyl ether was distilled to give a solid residue which was recrystallized from petroleum ether/ethyl acetate to give 6.7 g. of 3-ethylthio-5,6-bis(4-methoxyphenyl)-1,2,4-triazine, m.p. about 118°–120° C.

Analysis: $C_{19}H_{19}N_3O_2S$: Calc: C, 64.57; H, 5.42; S, 9.07: Found: C, 64.78; H, 5.24; S, 9.00.

EXAMPLES 4–6

The following compounds were prepared by the method of Example 3(B), using the appropriate alkyl halide (given in parenthesis after the compound name):

3-isopropylthio-5,6-bis(4-methoxyphenyl)-1,2,4-triazine (from isopropyl iodide), m.p. about 109°–111° C.

Analysis: $C_{20}H_{21}N_3O_2S$: Calc: C, 65.37; H, 5.76; S, 8.73: Found: C, 65.65; H, 5.53; S, 8.63.

3-hexylthio-5,6-bis(4-methoxyphenyl)-1,2,4-triazine (from hexyl bromide), m.p. about 92°–94° C., 7 g.

Analysis: $C_{23}H_{27}N_3O_2S$: Calc: C, 67.45; H, 6.65; S, 7.83; N, 10.26: Found: C, 67.66; H, 6.71; S, 8.00; N, 10.26.

3-benzylthio-5,6-bis(4-methoxyphenyl)-1,2,4-triazine (from benzyl chloride), m.p. about 128°–130° C., 10.3 g.

Analysis: $C_{24}H_{21}N_3O_2S$: Calc: C, 69.38; H, 5.09; S, 7.72: Found: C, 69.37; H, 5.19; S, 7.37.

EXAMPLE 7

Preparation of 3-Methoxy-5,6-bis(4-methoxyphenyl)-1,2,4-triazine (A) Procedure A Sodium, 3.0 g. (0.13 mole), was added piecewise under a nitrogen atmosphere to 100 ml. of dry methanol, followed by the addition of a slurry of 31.6 g. (0.1 mole) of 5,6-bis(4-methoxyphenyl)-3-methylthio-1,2,4-triazine in methanol. The reaction mixture was heated at reflux overnight. The reaction mixture was cooled and filtered. The filter cake and filtrate were extracted with diethyl ether. The diethyl ether was concentrated, giving a solid, m.p. >220° C. The solid was taken up in diethyl ether and the insoluble material was removed by filtration. The filtrate was dried over anhydrous sodium sulfate and concentrated to give a solid residue which was recrystallized from petroleum ether to give 3-methoxy-5,6-bis(4-methoxyphenyl)-1,2,4-triazine, m.p. about 105°–108° C.

Analysis: $C_{18}H_{17}N_3O_3$: Calc: C, 66.86; H, 5.30; N, 13.00: Found: C, 67.26; H, 5.97; N, 11.69.

(B) Procedure B

Sodium, 0.91 g. (0.04 mole), was added piecewise under a nitrogen atmosphere to 100 ml. of dry methanol, followed by the portionwise addition of 11.6 g. (0.036 mole) of 3-chloro-5,6-bis(4-methoxyphenyl)-1,2,4-triazine. The reaction mixture was heated at reflux for three hours, cooled, and stirred overnight. The reaction mixture was cooled and filtered. The filtrate was concentrated and the solid residue was crystallized from petroleum ether/ethyl acetate to give 8.5 g. of 3-methoxy-5,6-bis(4-methoxyphenyl)-1,2,4-triazine, m.p. about 135°–137° C.

Analysis: $C_{18}H_{17}N_3O_3$: Calc: C, 66.86; H, 5.30; O, 14.86; N, 13.00: Found: C, 66.84; H, 5.52; O, 14.86; N, 12.79.

EXAMPLE 8

The following compound was prepared by the method of Example 8(B), using ethanol in place of methanol:

3-ethoxy-5,6-bis(4-methoxyphenyl)-1,2,4-triazine, m.p. about 120°–122° C., 7.1 g.

Analysis: $C_{19}H_{19}N_3O_3$: Calc: C, 67.64; H, 5.68; O, 14.23; N, 12.46: Found: C, 67.92; H, 5.56; O, 14.43; N, 12.38.

What is claimed is:

1. The compound of the formula,

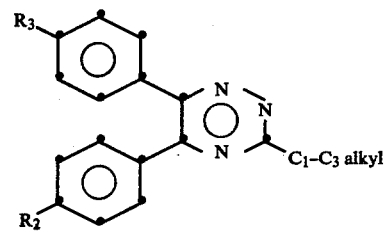

wherein
$R_2$ and $R_3$ independently are $C_1$–$C_3$ alkoxy or di($C_1$–$C_3$ alkyl)amino; and the pharmaceutically-acceptable acid addition salts of basic members thereof.

2. The compound of claim 1, wherein $R_2$ and $R_3$ are $C_1$–$C_3$ alkoxy and are the same.

3. The compound of claim 2, wherein $R_2$ and $R_3$ are methoxy.

4. The compound of claim 3, which compound is 5,6-bis(4-methoxyphenyl)-3-methyl-1,2,4-triazine.

5. The compound of claim 3, which compound is 3-ethyl-5,6-bis(4-methoxyphenyl)-1,2,4-triazine.

* * * * *